United States Patent [19]
Brown et al.

[11] 4,201,525
[45] May 6, 1980

[54] PERISTALTIC PUMP

[75] Inventors: Richard I. Brown, Northbrook; Roger L. Leaf, Antioch, both of Ill.

[73] Assignee: Baxter Travenol Laboratories, Inc., Deerfield, Ill.

[21] Appl. No.: 921,896

[22] Filed: Jul. 5, 1978

[51] Int. Cl.² .......................................... F04B 43/12
[52] U.S. Cl. .............................. 417/477; 417/DIG. 1
[58] Field of Search ................ 417/477, 476, DIG. 1

[56] References Cited

U.S. PATENT DOCUMENTS

| | | |
|---|---|---|
| 2,917,002 | 12/1959 | Mascaro . |
| 2,925,045 | 2/1960 | Mascaro . |
| 3,227,092 | 1/1966 | Clark ............................. 417/477 |
| 3,366,071 | 1/1948 | Dutler ........................... 417/477 |
| 3,644,068 | 2/1972 | Lepak ........................... 417/477 |
| 3,963,023 | 6/1976 | Hankinson ................... 417/477 |

FOREIGN PATENT DOCUMENTS 574621  4/1977  U.S.S.R. ................................. 417/477

Primary Examiner—Richard E. Gluck
Attorney, Agent, or Firm—Henry W. Collins; Paul C. Flattery; George H. Gerstman

[57] ABSTRACT

A peristaltic liquid pump in which a box-like housing encloses a rotatable head carrying a pair of rollers which engage a U-shaped portion of plastic tubing carrying liquid to be pumped. The housing has a light-transmissive cover member enabling the operator to view the tubing therein. A membrane is interposed between the rollers and the U-shaped portion of the plastic tubing, with the membrane having a relatively stiff surface for contacting the rollers and a relatively sticky surface for contacting the plastic tubing.

9 Claims, 2 Drawing Figures

PERISTALTIC PUMP

BACKGROUND OF THE INVENTION

This invention concerns an improved peristaltic liquid pump for external connection to plastic tubing carrying liquid to be pumped.

Although the present invention has particular utility with respect to the pumping of blood through plastic tubing, it is to be understood that it may be used advantageously with other liquids to be pumped.

An object of the present invention is to provide a peristaltic pump which is simple in construction and easy to manufacture.

Another object of the present invention is to provide a peristaltic pump which is simple to load and to clean.

A further object of the present invention is to provide a peristaltic pump which enables the operator to view the tubing located therein.

Another object of the present invention is to provide a peristaltic pump which utilizes a membrane interposed between the pump's rollers and the tubing which membrane prevents the tubing from migrating and gives long life to the rollers.

Other objects and advantages of the present invention will become apparent as the description proceeds.

BRIEF DESCRIPTION OF THE INVENTION

In accordance with the present invention, a peristaltic liquid pump is provided for external connection to plastic tubing carrying liquid to be pumped. The pump includes a housing adapted for receiving a U-shaped portion of the plastic tubing. The housing includes a main roller portion and a cover portion connected to the main roller portion.

A rotatable head is located within the main roller portion, and a pair of rollers are connected to the rotatable head and are located to face the cover portion when the cover portion is closed. The rollers are rotatably connected to the rotatable head and the rotatable head is coupled to an electric motor.

The housing defines means for receiving the U-shaped portion of the plastic tubing so that the U-shaped portion will overlie the rollers during rotation of the rotatable head. A membrane is interposed between the rollers and the U-shaped portion of the plastic tubing. The membrane has a relatively stiff surface for contacting the rollers and a relatively sticky surface for contacting the plastic tubing.

In the illustrative embodiment, the main roller portion of the housing comprises a rectilinear box-like structure enclosing all but one face of the rotatable head and rollers. The cover portion is light-transmissive to enable the operator to view the tubing therein.

In the illustrative embodiment, a hinge connects the cover portion to the main roller portion and enables pivoting of the cover portion with respect to the main roller portion about an axis substantially perpendicular to but offset from the axis of rotation of the head.

In the illustrative embodiment, the membrane comprises a pair of connected plastic layers. The layer which has a relatively stiff surface comprises Hytrel ® polyester elastomer and the other layer which has a relatively sticky surface comprises polyvinyl chloride.

A more detailed explanation of the invention is provided in the following description and claims, and is illustrated in the accompanying drawings.

BRIEF DESCRIPTION OF THE INVENTIONS

FIG. 1 is a top plan view of a peristaltic liquid pump constructed in accordance with the principles of the present invention, with the cover portion in its open position; and FIG. 2 is a cross-sectional view thereof, taken along the plane of the line 2—2 of FIG. 1.

DETAILED DESCRIPTION OF THE ILLUSTRATIVE EMBODIMENT

Figure 1:
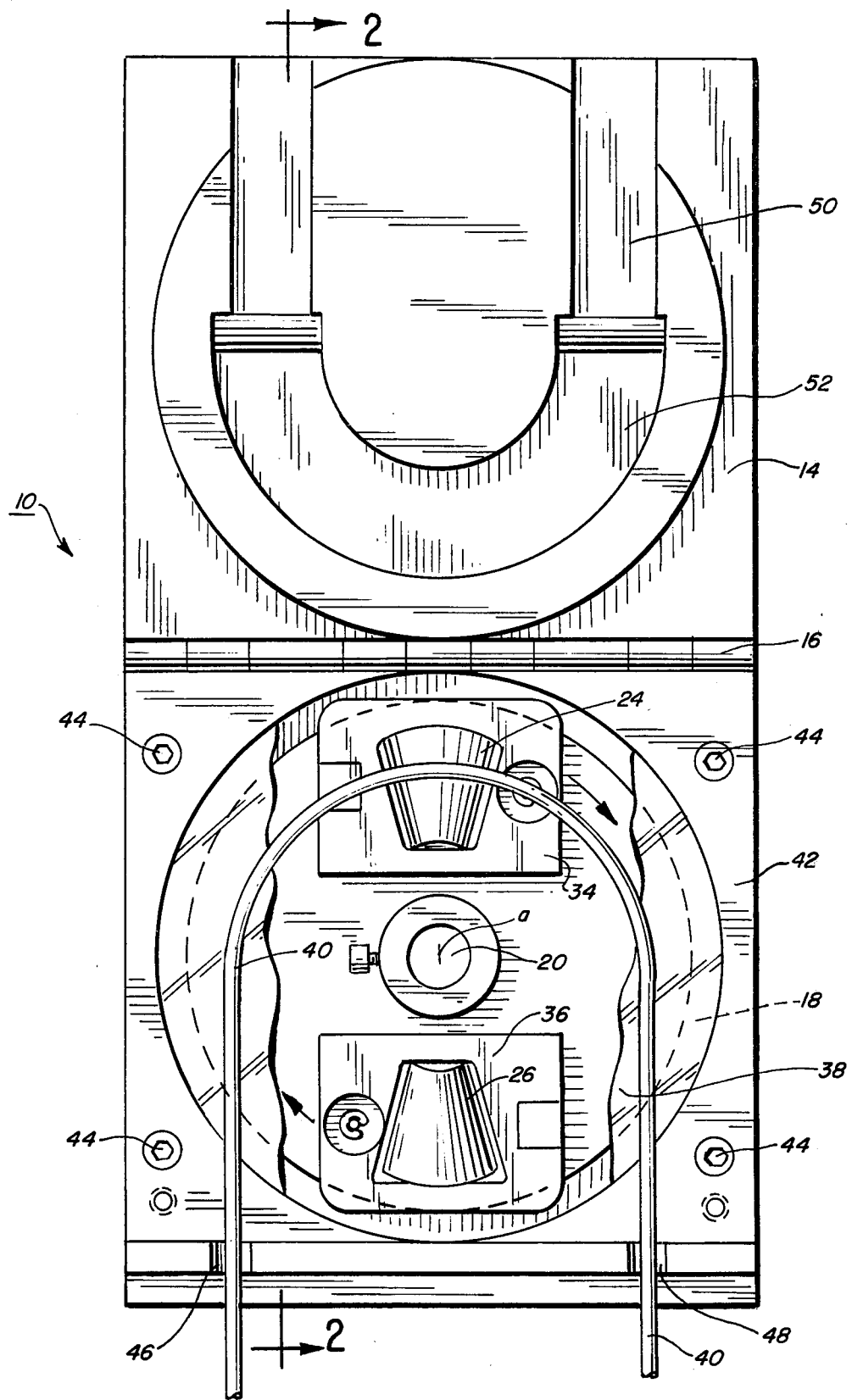
Figure 2:
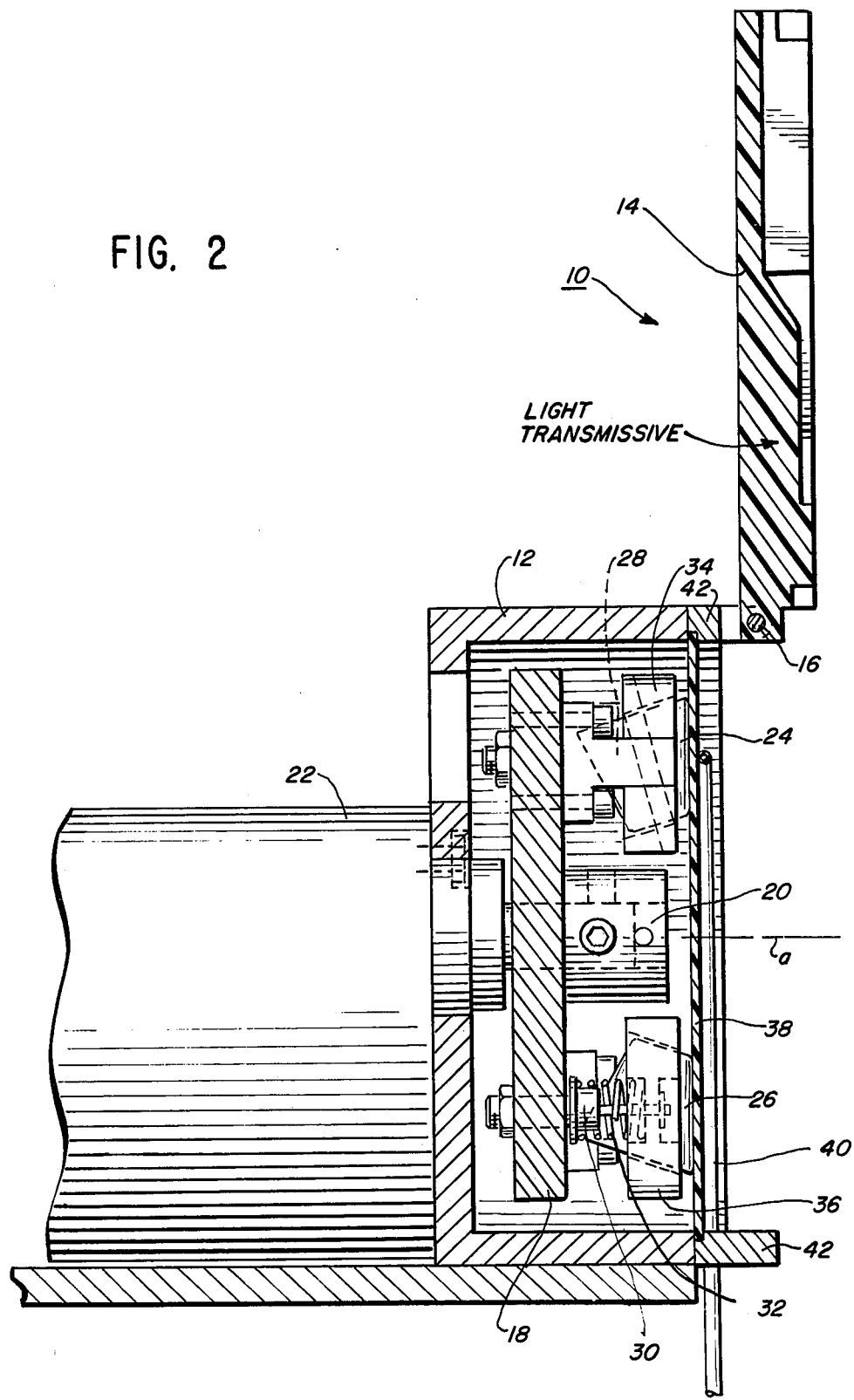

Referring to the drawings, a peristaltic pump is illustrated therein having a main housing 10 comprising a main roller portion 12 and a cover portion 14 pivotally connected thereto by means of a hinge 16. The main roller portion 12 is preferably of rectilinear, box-shaped construction and encloses a rotatable head 18 which is coupled by shaft 20 to an electric motor 22, thus providing rotation of head 18 about axis a.

It can be seen that cover member 14 is hinged to pivot about an axis that is perpendicular to but offset from axis a, whereby the cover member acts to cover the opening of the box-shaped main roller portion 12.

A pair of rollers 24, 26 are resiliently and pivotally coupled to head 18. Rollers 24, 26 have a truncated conical shape and are mounted by means of arms 28, 30, respectively, which carry springs 32 to enable rollers 24, 26 to move resiliently with respect to head 18 in a direction that is parallel to axis a. Arms 28, 30 carry shaft housings 34, 36, respectively, which have shafts enabling rollers 24, 26 to rotate about their respective central axes.

A membrane 38 is interposed between the rollers 24, 26 and the plastic tubing 40 with which the pump reacts. Membrane 38 is held in place by means of a cover pate 42 that is fastened to main roller portion 12 by means of suitable fastening means 44.

Membrane 38 is formed of a suitable material to prevent the tubing 40 from migrating during operation of the pump, yet at the same time to protect rollers 24 and 26 and extend the life of the rollers. To this end, the membrane 38 has a relatively stiff surface for contacting rollers 24, 26 and a relatively sticky surface for contacting the plastic tubing 40. It has been found that an effective membrane material comprises a pair of connected plastic layers, laminated or the like, with the one layer forming the relatively stiff surface comprising Hytrel ® polyester elastomer and the other layer having the relatively sticky surface comprising polyvinyl chloride.

As shown in FIG. 1, tubing 40 is given a U-shaped configuration so as to overlie one of the rollers (roller 24 in FIG. 1). In order for tubing 40 to be properly held in place, main roller housing 12 defines a pair of grooves 46, 48 and cover portion 14 defines a U-shaped recess 50 which overlies the U-shaped portion of tubing 40. The bight 52 of the U-shaped recess 50 is not as recessed as other portions of the U-shaped recess 50, so that bight portion 52 will act to urge the looped portion of tubing 40 against the roller.

It can be seen that when motor 22 is actuated, head 18 will rotate thus effectively rotating rollers 24, 26 about axis a and the rollers 24, 26 will rotate about their own axes as they underlie the loop portion of tubing 40, thereby providing the peristaltic pumping action. The pump is very simply loaded by merely looping plastic tubing 40 in the position shown in FIG. 1 while the cover is open, and once looped into position, cover portion 14 is closed over the tubing and the motor 22 is actuated. Because of the unique construction of the peristaltic pump just described, in addition to the device being easy to load it is extremely easy to clean and the membrane operates to prevent the tubing 40 from migrating and to give extended life to the rollers.

Cover portion 14 is preferably transparent or sufficiently light-transmissive so as to enable the operator to view tubing 40 during operation of the device. In this manner, the operator can view any failure that may occur, such as air bubbles, tube breakage or loss of liquid flow.

Although an illustrative embodiment of the invention has been shown and described, it is to be understood that various modifications and substitutions may be made by those skilled in the art without departing from the novel spirit and scope of the present invention.

What is claimed is:

1. A peristaltic liquid pump for external connection to plastic tubing carrying liquid to be pumped, which comprises:
   a housing adapted for receiving a U-shaped portion of the plastic tubing, said housing including a main roller portion and a cover portion connected to said main roller portion;
   a rotatable head located within said main roller portion;
   a pair of rollers connected to said rotatable head and located with their roller surfaces facing said cover portion when said cover portion is closed;
   means rotatably connecting said rollers to said rotatable head;
   means for coupling said rotatable head to an electric motor;
   means defined by said housing for receiving the U-shaped portion of the plastic tubing so that the U-shaped portion will overlie the rollers during rotation of said rotatable head;
   a membrane comprising a sheet overlaying said main roller portion of said housing between said rollers and the U-shaped portion of the plastic tubing, said membrane having a relatively stiff surface for contacting said rollers and a relatively sticky surface for contacting said plastic tubing; and
   said cover portion being constructed to overlie said rollers, membrane and U-shaped portion of the plastic tubing and to urge the U-shaped portion of the tubing against the membrane and a roller when the cover portion is closed.

2. A peristaltic liquid pump as described in claim 1, said main roller portion of the housing comprising a rectilinear box-like structure enclosing all but one face of said rotatable head and rollers.

3. A peristaltic liquid pump as described in claim 1, said cover portion being light-transmissive to enable the operator to view the tubing therein.

4. A peristaltic liquid pump as described in claim 1, said rotatably connecting means including a spring connected between each of said rollers and said head for biasing the rollers against the plastic tubing resiliently.

5. A peristaltic liquid pump as described in claim 1, said U-shaped portion receiving means comprising a pair of grooves defined by said main roller portion and a U-shaped recess defined by said cover portion.

6. A peristaltic liquid pump as described in claim 1, said membrane comprising a pair of connected plastic layers, with one layer which has a relatively stiff surface comprising Hytrel ® polyester elastomer and the other layer which has a relatively sticky surface comprising PVC.

7. A peristaltic liquid pump as described in claim 1, including a hinge connecting said cover portion to said main roller portion and enabling pivoting of said cover portion with respect to said main roller portion about an axis substantially perpendicular to but offset from the axis of rotation of said head.

8. A peristaltic liquid pump for extenal connection to plastic tubing carrying liquid to be pumped, which comprises:
   a housing adapted for receiving a U-shaped portion of the plastic tubing, said housing including a main roller portion and a cover portion connected to said main roller portion;
   a hinge connecting said cover portion to said main roller portion and enabling pivoting of said cover portion with respect to said main roller portion;
   said main roller portion of the housing comprising a rectilinear box-like structure and said cover portion being light-transmissive to enable the operator to view the tubing therein;
   a rotatable head located within said main roller portion;
   a pair of rollers connected to said rotatable head and located with their roller surfaces facing said cover portion when said cover portion is closed;
   means rotatable connecting said rollers to said rotatable head, said rotatably connecting means including a spring connected between each of said rollers and said head for biasing the rollers against the plastic tubing resiliently;
   means for coupling said rotatable head to an electric motor;
   means defined by said housing for receiving the U-shaped portion of the plastic tubing so that the U-shaped portion will overlie the rollers during rotation of said rotatable head, said U-shaped portion receiving means comprising a pair of grooves defined by said main roller portion and a U-shaped recess defined by said cover portion;
   a membrane comprising a sheet overlaying said main roller portion of said housing between said rollers and the U-shaped portion of the plastic tubing, said membrane having a relatively stiff surface for contacting said rollers and a relatively sticky surface for contacting said plastic tubing; and
   said cover portion being constructed to overlie said roller, membrane and U-shaped portion of the plastic tubing and to urge the U-shaped portion of the tubing against the membrane and a roller when the cover portion is closed.

9. A peristaltic liquid pump as described in claim 8, said membrane comprising a pair of connected plastic layers, with one layer which has the relatively stiff surface comprising Hytrel ® polyester elastomer and the other layer which has the relatively sticky surface comprising PVC.

* * * * *